United States Patent [19]

Makoui et al.

[11] Patent Number: 5,139,841

[45] Date of Patent: Aug. 18, 1992

[54] SUPERABSORBENT TOWEL WITH SCRIM REINFORCEMENT

[75] Inventors: Kambiz B. Makoui, Menasha; David H. Hollenberg, Neenah; Ralph H. Reeves, Appleton, all of Wis.

[73] Assignee: James River Corporation of Virginia, Richmond, Va.

[21] Appl. No.: 676,297

[22] Filed: Mar. 27, 1991

[51] Int. Cl.[5] .......................... B32B 5/08; B32B 5/26; B32B 31/12; B32B 31/20

[52] U.S. Cl. .................................. 428/109; 156/273.7; 156/275.5; 156/281; 156/307.3; 156/307.7; 156/313; 156/324; 428/110; 428/219; 428/240; 428/255; 428/283; 428/286; 428/287; 428/299; 428/340; 604/365; 604/367; 604/372; 604/378; 604/383

[58] Field of Search ................. 156/273.7, 275.5, 281, 156/307.3, 307.7, 313, 324; 428/109, 110, 240, 219, 255, 283, 286, 287, 299, 340; 604/365, 367, 372, 378, 383

[56] References Cited

U.S. PATENT DOCUMENTS

| | | | |
|---|---|---|---|
| 4,001,472 | 1/1977 | Thomas et al. | 428/109 |
| 4,540,625 | 9/1985 | Sherwood | 428/283 |
| 4,762,968 | 2/1988 | Hayashi et al. | 428/264 |
| 4,820,560 | 4/1989 | Buckwald et al. | 428/283 |
| 4,842,927 | 6/1989 | Itoh et al. | 428/264 |
| 4,902,559 | 2/1990 | Eschway et al. | 428/283 |
| 4,948,659 | 8/1990 | Itoh et al. | 428/264 |

Primary Examiner—James C. Cannon
Attorney, Agent, or Firm—William A. Aguele; Richard J. Gallagher; Thomas H. Whaley

[57] ABSTRACT

A disposable, cloth-like towel of superior wet strength and absorbency comprises a scrim coated with a superabsorbent material, with one or more nonwoven fibrous webs bonded to the coated scrim. The superabsorbent coating preferably is formed by wetting the scrim with water or an aqueous adhesive, applying a solid hydrophilic polymer to the scrim, then applying a nonwoven absorbent cellulosic web to the coated scrim and drying the resulting composite laminate. Bonding of the scrim to the nonwoven fibrous web can be achieved by applying an adhesive to the side of the cellulosic web which is brought into contact with the coated scrim. Alternatively, both the hydrophilic coating and bonding can be effected by sandwiching the scrim, coated with an unreacted mixture of hydrophilic polymer and crosslinking compound, between the two fibrous layers and then subjecting the multi-ply laminate sheet to crosslinking reaction conditions to form the superabsorbent on the scrim as well as to cause adhesion of the nonwoven fibrous webs thereto.

18 Claims, 1 Drawing Sheet

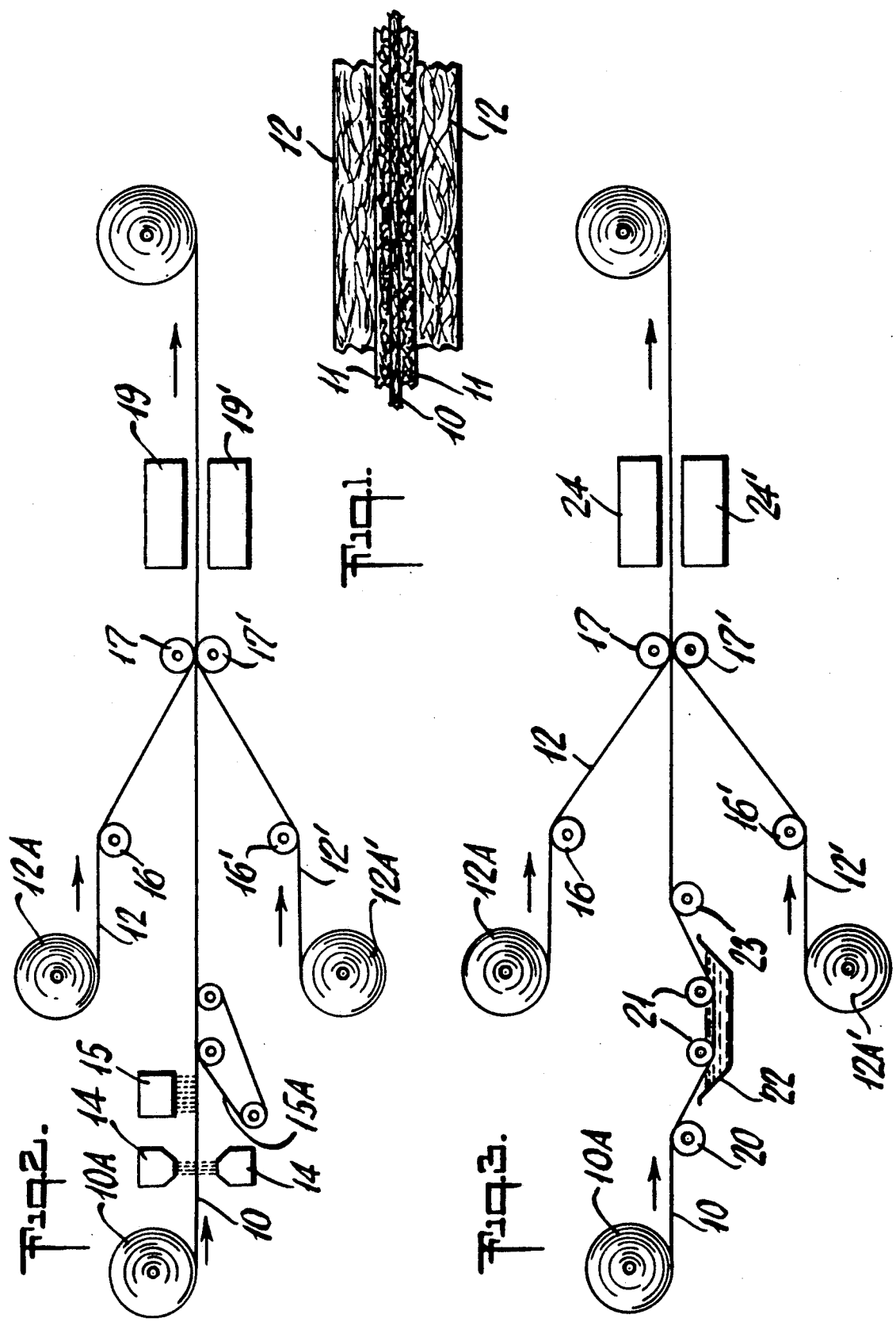

SUPERABSORBENT TOWEL WITH SCRIM REINFORCEMENT

This invention relates to a superabsorbent cloth-like laminate structure and to its method of preparation. In one of its more specific aspects, this invention relates to a scrim-reinforced, cloth-like, composite liquid absorbent laminate structure comprising a superabsorbent material associated with scrim and covered on at least one side with a nonwoven fibrous web. In one of its still more specific aspects, the invention includes a scrim-reinforced composite laminate in which the scrim is coated with solid absorbent and sandwiched between layers of non-woven cellulosic webs. Other aspects of this invention relate to the method of manufacture of the structure and to consumer products incorporating such structures as an element thereof. The resulting structures are both highly absorbent and resistant to tear.

BACKGROUND OF THE INVENTION

The novel cloth-like fibrous laminate is useful as disposable toweling, bed pads, diaper liners, sanitary napkins, wipes, wound dressings, and filter materials which are capable of removing moisture from non-aqueous filtrates. In one of its referred embodiments, a composite fabric comprising a superabsorbent scrim layer sandwiched between layers of dry laid nonwoven cellulosic fibers is produced as a strong laminate structure of high liquid-absorbency which is soft to the touch.

Numerous proposals have been made for the manufacture of cellulosic composite products useful as disposable towels and similar products. Two desirable properties of such absorbent products, namely, high-liquid absorbency and superior wet strength are virtually antithetical. High absorbency is usually associated with a fibrous structure of high porosity but low tensile strength, whereas wet strength usually involves the use of binders or compacted fibers exhibiting relatively low absorbency.

A method for the manufacture of a cloth-like composite laminate is disclosed in U.S. Pat. No. 4,634,621 to Manning et al, in which scrim coated with a thermoplastic binder is inserted between two non-woven layers bonded with a latex adhesive and the composite heated to a temperature sufficient to activate the thermoplastic binder. A scrim reinforced, cloth-like composite laminate is produced having both excellent dry and wet strength properties.

A number of patents are directed to methods for incorporating superabsorbent materials, commonly referred to in the art as SAM's, into cellulosic composites to form products of greatly enhanced absorbency for liquids. For example, Korpman, U.S. Pat. No. 4,413,995 discloses an absorbent panel structure useful in various hygienic products in which a paper or fabric substrate is coated with a reactive composition of a liquid polyhydroxy organic compound and a particulate water-insoluble, water swellable absorbent polymer. Watt, in U.S. Pat. No. 4,600,462, discloses a latex bonded, air laid web of enhanced absorbency to which a water soluble hydrophile is added and dried on the web. An absorbent pad assembly in which a hydrophilic polymer coating is applied to one surface of one pad and covered with another pad adjacent the coated surface is disclosed in U.S. Pat. No. 4,461,621 to Karami et al.

In accordance with this invention, a strong disposable absorbent laminate of improved water absorbency is formed by incorporating a superabsorbent material on a polyester or fiberglass scrim and covering the scrim with a layer of cellulosic or synthetic fibers. In one specific embodiment of the invention, the scrim is coated with an adhesive, e.g. a polyvinyl alcohol latex, to which superabsorbent powder is added to form a coating on one or both sides of the scrim, and the thus formed superabsorbent scrim is covered with a web of cellulosic fibers. The resultant product is a strong laminate structure with superior water absorbency and a cloth-like appearance and feel.

In accordance with a preferred embodiment of this invention, a cloth-like composite laminate is formed which comprises two nonwoven layers of cellulosic fibers attached to the opposite sides of a scrim or screen which has been coated or impregnated with a superabsorbent hydrophilic polymer.

A number of superabsorbent polymers are known in the art. U.S. Pat. No. 4,600,458 to Kramer et al., for example, includes a long list of patents disclosing superabsorbent polymers useful in absorbent structures in which the superabsorbent polymers are incorporated into an absorbent fibrous web or laminate. Among the polymers disclosed for this purpose are saponified starch-polyacrylonitrile graft copolymers, crosslinked/-grafted cellulose, saponified vinyl acetate-acrylic acid copolymers, starch grafted polyvinyl acetate, acrylic acid polymers, crosslinked polyethylene oxide, and the like. In the method of this patent, superabsorbent solid particles are layered between webs of fibrous material and the layered stacks of webs crimped to retain the solid absorbent in place. McFarland et al., U.S. Pat. No. 4,655,757 incorporates solid particles of superabsorbent material into a coformed layer of meltblown fibers containing wood fibers for improved absorbency. Among the superabsorbents mentioned therein are those formed from hydrolyzed cross-linked polyacrylamides, polyacrylates, polymers of acrylic polymers of their copolymers. Sodium polyacrylate hydrocolloid particles are preferred as superabsorbents.

Fibrous silvers and absorbent structures having superabsorbents or hydrocolloids distributed therethrough are disclosed in U.S. Pat. Nos. 4,340,556 to Ciencewicki and 4,596,567 to Iskra wherein some superabsorbents are described as having a backbone of natural or synthetic polymers with hydrophilic groups, or polymers containing hydrophilic groups, chemically bonded thereto or in intimate admixture therewith. Among the superabsorbents mentioned therein are modified natural and regenerated polymers, such as polysaccharides including cellulose, and starch and regenerated cellulose which are modified by being carboxylated, phosphonoalkylated, sulfoalkylated, or phosphorylated to render them highly hydrophilic. These polymers may be cross-linked to render them water insoluble, all as described in U.S. Pat. No. 4,105,033 to Chatterjee et al.

The superabsorbent polymer and cross linker may be any of those already known in the chemical literature as well as those resulting from continued research and development to produce water insoluble cross linked polymer products of enhanced hydrophilic propensity. Currently, superabsorbents suitable for application to the scrim used in the toweling of this invention include the metal ion crosslinked polymers described in U.S. Pat. No. 4,090,013 and a polyacrylate absorbent containing both amide and carboxylate groups prepared by radiation polymerization and crosslinking as described in U.S. Pat. No. 4,192,727. Hydrophilic polymers that are reacted with organic crosslinkers as described in the U.S. Pat. No. 4,310,593 are further examples of superabsorbents that may be applied to the scrim.

The scrim is formed of a continuous filament of nonwoven material such as rayon, nylon, polyester, polypropylene, aramids, and glass. A polyester scrim or screen sold under the trademark Bayex by Bay Mills, Ltd., of Canada is illustrative of a desirable reinforcement for production of the novel toweling of high wet strength and superior water absorbency. The scrim will in most cases have a mesh opening of 2 to 5 mm between fibers and will contribute a weight in the range of 0.2 to 2.0 ounces per square yard to the total weight of the multi-ply towel.

The two layers of nonwoven cellulosic fibers which are attached to the opposite sides of the superabsorbent coated scrim or screen may be produced by any of the many known procedures. For example, previously mentioned U.S. Pat. No. 4,634,621, incorporated herein by reference, discloses an operation in which dry fibers are laid on two separate belts and bonded with a latex adhesive forming two separate air laid bonded cellulosic webs which are then brought into contact with the opposite sides of a scrim coated with a thermoplastic resin. In the process of this patent, the scrim has a thermoplastic polymer binder applied as a coating to each of its two sides. The nonwoven cellulosic layers and the intermediate binder-coated scrim are finally passed through a heated lamination station to cause adhesion of the cellulosic layers to the scrim.

In accordance with a preferred embodiment of this invention, each of the cellulose webs which is brought into contact with the scrim is given a coating of binder on its surface nearest the scrim so that surface fibers of each nonwoven layer become attached on contact with the superabsorbent scrim and on curing of the binder, the cellulosic layers are bonded to the scrim to provide a unitary product of high wet strength and greatly enhanced absorbency.

Alternatively, it is in many cases preferable to bring the nonwoven cellulosic layers into contact with the scrim immediately after the hydrophilic polymer has been applied thereon. In such cases, the wet surface coating on the scrim contacts the cellulosic layers and during the drying or curing reaction creates a bonding of the cellulosic layers to the scrim.

BRIEF DESCRIPTION OF THE DRAWINGS

To facilitate the further description and understanding of the invention, reference will be made to the accompanying drawings in which:

FIG. 1 is a fragmentary sectional view of the multi-ply cloth like laminate of the invention;

FIG. 2 is a schematic diagram showing the apparatus used in the method of making the product illustrated in FIG. 1; and FIG. 3 is a schematic diagram showing alternative apparatus for the manufacture of a superabsorbent product by the method of this invention.

DESCRIPTION OF PREFERRED EMBODIMENTS

A typical cross section of the product of the invention is illustrated in FIG. 1 wherein scrim 10 coated on both sides with superabsorbent material 11 is sandwiched between, and bonded to, the nonwoven cellulosic webs 12. The superabsorbent material 11 on the opposite sides of scrim 10. The inner surfaces of cellulosic layers 12 contiguous to scrim 10 bond to the coated scrim to provide a disposable, cloth-like towel of superior absorbency and wet strength.

The nonwoven cellulosic webs 11 may be formed from air laid cellulose fibers by methods well known in the art, for example, by the method and apparatus disclosed in U.S. Pat. No. 3,797,074; U.K. Patent 2,008,638B; or U.S. Pat. Nos. 4,014,635; 4,193,751; and 4,285,647, incorporated by reference herein.

With reference to FIG. 2, scrim 10 from roll 10A is passed between sprays 14 which apply water or a suitable adhesive, e.g. an aqueous solution of carboxymethyl cellulose, to both sides of the scrim. The wetted scrim 10 then passes through station 15 where powdered superabsorbent material is added to the scrim. The powdered superabsorbent adheres to the wet scrim. In this specific embodiment, the scrim passes over a belt 15A, which presses solid absorbent material passing through openings in the scrim against the side opposite the powder applicator 15. Both sides of the scrim are coated with superabsorbent powder which is held in place by the water or adhesive on the scrim.

Simultaneously, two nonwoven latex bonded air laid cellulosic webs 12 and 12' are supplied from a suitable source over rollers 16 and 16' into the nip of opposed rollers 17 and 17' where they meet and sandwich scrim 10 laden with superabsorbent 11 between them. The multi-ply sheet then passes through drying station 19 which hastens the bonding of fibrous layers 12 and 12' to absorbent-coated scrim 10.

In FIG. 3, illustrating apparatus similar to that of FIG. 2, scrim 10 passes over roller 20 and under rollers 21 which are partially immersed in a liquid polymer superabsorbent precursor in tank 22. The thus impregnated scrim 10 is then drawn from tank 22 over roller 23, and fed into the nip of opposed rollers 17 and 17' where it is sandwiched between nonwoven fibrous webs 12 and 12'. Thence, the multi-ply sheet passes through station 24 crosslinking the polymer precursor thus forming the superabsorbent polymer and bonding the cellulosic layers 12 to the opposite sides of scrim 10 by heat of ionizing radiation.

The weight of the cellulosic fibers forming each nonwoven layer or web is within the range of 10 pounds per 3000 square feet ream to 90 pounds per ream. The separate layers containing the cellulosic fibers can be formed by air laying the cellulosic fibers onto a foraminous belt as well known in the art. One type of apparatus for air forming each layer of cellulosic fibers is shown in U.S. Pat. No. 4,193,751 to Miller. Other techniques for forming nonwoven fibrous webs, known in the art, can also be used. Foam forming as described in U.S. Pat. No. 3,837,999 to Chung or forming an air emulsion as disclosed in U.S. Pat. No. 4,049,491 to Brandon et al are suitable as is conventional web formation processes employing an aqueous slurry of fibers. The webs may comprise synthetic fibers and may be subjected to hydroentanglement prior to lamination with the polymer coated scrim.

When the webs are formed by an air laying process, the adhesive, used to bind together the cellulosic fibers in each nonwoven layer can be selected from various latex adhesives known in the art. Acceptable latex adhesives include acrylate emulsions, butadiene-styrene emulsions, ethylene-vinyl acetate emulsions, and acrylonitrile-butadiene emulsions. An especially effective latex adhesive is an ethylene-vinyl acetate emulsion marketed under the tradename Airflex A-106 by Air Products, Inc. of Pennsylvania. The skilled artisan can select a particularly preferred latex adhesive for this application, depending upon the type of cellulosic fibers that are to be bonded. The latex adhesive is applied by known techniques, e.g., by spraying or foaming. The amount of solids deposited from the latex adhesive depends, inter alia, on the weight of the cellulosic fibers in each layer. Generally, latex adhesives having from 15 to 25% solids are used. After the latex adhesive is applied to the fibers, it may be dried by conventional techniques. In a preferred embodiment of this invention, two separate nonwoven layers of latex bonded cellulosic fibers are employed, one on each side of the superabsorbent coated scrim, as illustrated in the accompanying drawings.

The scrim is preferably a continuous filament scrim composed of a nonwoven mesh material. Examples of suitable materials are filaments of nylon, rayon, polyester, polypropylene, glass, and aramids, such as Kevlar and Nomex which are trademarks of the E.I. DuPont de Nemours & Co. The weight of the scrim is preferably within the range of 0.2 ounce per square yard to 2.0 ounces per square yard. Other scrims, such as a mesh scrim, can also be used in the present invention. An example of a bonded polyester nonwoven material useful as scrim is marketed under the tradename Bayex, by Bay Mills, Ltd. In the following examples, Bayex scrim having the dimensions of 4 threads per inch of 150 denier in the cross machine direction (CD) and 12 threads per inch of 70 denier in the machine direction (MD) is employed.

A preferred nonwoven material for the scrim has a set of spaced machine direction threads with a second set of spaced threads lying cross-directionally with respect to the first set of threads. The two sets of threads are bonded or adhered together at the points where the threads of one set cross the threads of another set. The threads making up the scrim can be in an over and under configuration, as shown in U.S. Pat. No. 3,885,279 to Darnell et al, or a one side pattern, as shown in U.S. Pat. No. 2,902,395 to Hirschy et al. Other scrim configurations known in the art, such as extended netting described in U.S. Pat. No. 4,152,479 to Larsen, can also be used.

In an alternate embodiment one side of each of the nonwoven fibrous webs is coated with a binder so that the two nonwoven layers of fibers adhere to the superabsorbent coated scrim, when the scrim is sandwiched between the two nonwoven fibrous layers. Examples of acceptable polymer binders includes polyvinyl chloride plastisols, polyvinyl chloride, polyvinyl acetate, ethylene acrylic acid and ethylene vinyl acetate. Other known binders can also be used. An especially effective polyvinyl chloride plastisol is marketed under the tradename Bayex F-50 by the Bay Mills, Ltd. of Canada.

The skilled artisan can select the particular monomer, the polymer, or latex type binder desired depending upon the characteristics of the fibers and the superabsorbent coated scrim that are to be bound together. The scrim can be coated with the thermoplastic polymer binder by various known techniques.

After the scrim is inserted between the two nonwoven layers of absorbent or nonabsorbent fibers, the composite laminate comprising the scrim and the two nonwoven fibrous layers is subjected to drying, if required, and when using a thermoplastic binder, heated to a temperature sufficient to activate the thermoplastic binder. The heating of the scrim and the nonwoven layers may be carried out with or without pressing the composite laminate comprising the scrim and the nonwoven layers. The composite laminate typically will have a basis weight in the range of from about 80 to 300 pounds per 3000 sq. ft. ream.

In an alternate embodiment of this invention, the scrim is coated with a liquid monomer or polymer precursor and cross-linked in situ to produce the hydrophilic polymer coating of the scrim. Those skilled in the art known that there are numerous hydrophilic polymers which may be crosslinked with or without crosslinking agents and which are suitable for use to provide the superabsorbent coating on the scrim pursuant to this invention. U.S. Pat. No. 4,461,621 list several patents which teach the formation of superabsorbent coatings that are useful in the present invention. Ionizing radiation may be used to accelerate the cross-linking reaction with or without the application of heat from an external source.

EXAMPLES

In the following examples, the above described laminates were tested for maximum absorption capacity and retention under load of water (Examples 1 to 5, 1A to 5A, and 6 to 8) and of a one weight percent aqueous saline solution test fluid (Examples 6A to 8A) using a device known in the industry as an Automated Gravimetric Absorbency Tester (AGAT), also known as a Gravimetric Absorbency Tester (GAT). To perform this test, a dry specimen of known weight and size is placed on a porous plate of the tester and allowed to absorb the test fluid to its maximum capacity. The amount of liquid test fluid absorbed by the specimen is measured and recorded as grams of liquid absorbed per gram of specimen under test. The initial absorption rate in grams of liquid absorbed per gram of test specimen per second and the volume change of the specimen, i.e. the percentage expansion or contraction of the specimen which takes place due to absorption of the test liquid are determined and recorded. The test fluid is supplied to the sample from a container, which is placed over a balance through a glass porous plate. Therefore, the fluid absorbed by the sample through the porous plate is reflected by the display change in the balance and recorded by a computer. When the absorption stabilizes, and the balance gives the same reading over a 15 second interval, this portion of the test is complete. To prevent flooding of the sample with the test fluid, the porous plate height is set at a slightly negative hydrostatic tension (1.5 centimeter) over the water reservoir. This permits the sample to absorb as much fluid as it will take up (demand wetability test) without flooding the sample.

The next property measured is the retention value at a higher hydrostatic head. In this routine, the amount of fluid that drains out of the sample, once the porous plate has been raised to a specified height is measured under "no load" conditions. For the glass plates with pore size of 50 microns, the height used is 26 centimeters.

The water absorption ratio is calculated from the known weight of the sample and the measured weights of water absorbed and water retained by the sample. In the following tables, the absorption and retention values are reported as grams of water per gram of sample.

EXAMPLES 1-5

Scrim reinforced superabsorbent laminates were prepared in accordance with the above-described method of this invention using Bayex brand scrims having 4×4 threads per inch and 6×3 threads per inch and basis weights of about 10 g/m². The scrims were coated with the indicated superabsorbent polymers and laminated between two air laid, latex bonded cellulose webs. The control specimens are laminates containing no superabsorbent. Specimens containing solid superabsorbents were made up using the same components and in the same basis weights as in the control specimens with "heavy" and "light" loads of SANWET IM-1500 a superabsorbent powder marketed by Hoechst Calanese Company and with a superabsorbent powder marketed under the trade name NORSOCRYL B-65 by Norsolor.

To produce these specimens, the scrim was wetted with deionized water and then coated with the superabsorbent powder by a Nordson powder gun. The superabsorbent powder adhered to the wetted surface of the scrim. The add-on weight of the superabsorbent powder on the scrim was controlled by the regulation of the amount of water added to the scrim and by the mesh size of the scrim. Within limits, the amount of powder retained on the scrim, i.e. the wetter the scrim, the more sticks to it thus raising the weight of the specimen. After coating, the scrim containing the superabsorbent was sandwiched between two airlaid cellulose web substrates. A confining pressure of 100 g/cm² was applied to the specimens bonding the layers together. The "light weight" specimens of Table 1 contained an add-on weight of superabsorbent in the range of 35 to 55 grams per 100 grams of laminated carrier (scrim and airlaid substrates). The "heavy weight" specimens contained an add-on weight in the range of 188 to 210 g superabsorbent per 100 grams composite substrate carrier. The indicated basis weights of the specimens in grams per square meter (g/m²) represent the total basis weights of the composite laminates.

The prepared specimens were tested (two replicates A and B) for maximum absorption capacity by the porous plate method using a 1% saline solution as a test media. Absorbency results (Table 1) show that the specimens containing superabsorbent powder have a considerably higher capacity per square meter as compared with the control specimens.

of cellulosic webs was prepared as follows. A hydrophilic superabsorbent material precursor (superabsorbent 19) was prepared from 54 grams Acrysol A-3 (an aqueous dispersion of a polyacrylate containing about 25 weight percent solids) partially neutralized by the addition of 4.9 grams sodium hydroxide. Sufficient ammonium hydroxide was added to bring the pH of the dispersion from below 7 to about 7.5. Then 9 grams of ammonium carbonate is added. The resultant pH should be 8 or higher. The pH of the solution is further adjusted, if necessary, to a pH of 8 or higher by the addition of further amounts of ammonium hydroxide. To this dispersion is added 4.5 grams ammonium zirconium carbonate (20 weight percent solids) as a crosslinking agent.

Bayex scrim having 6×3 ends per inch was coated with the above-described precursor and sandwiched between two layers of an air laid web of softwood fibers to produce superabsorbent 19 of Examples 7 and 7A of Tables 2 and 3. The composite laminate of Example 7 is heated to remove moisture and crosslink the polyacrylate polymer superabsorbent precursor. As indicated in Table 2, The add-on amount of superabsorbent in Example 7 amounts to 6.8 grams per square meter and in Example 7A, to 5.9 grams per square meter. The control specimens, 6A and 6B are produced from the same scrim and air laid webs as for Examples 7 and 7A without superabsorbent.

Composite laminates comprising a superabsorbent coated scrim sandwiched between two nonwoven cellulose webs were prepared as in Examples 2 to 5. In this case, (Examples 8 and 8A) a very heavy coating of superabsorbent fiber marketed under the trade name Fibersorb SA 7000 by ARCO Chemical Company was adhered to the scrim by wetting the scrim with water as described hereinabove and coating the scrim with superabsorbent fibers. The coated scrim was sandwiched between two cellulose webs coated with adhesive and bonded by passing the laminate between press rolls and drying.

The absorbency results for specimens for Examples 7, 7A, 8 and 8A scrims coated with the crosslinked polymer of fiber are shown in Tables 2 and 3. The absorbency test data of these products was measured by the porous plate method using water as the test media and reported in Table 2. Comparative data obtained by the porous plate method using 1% saline solution as the absorption test media (Examples 7A and 8A) are reported in Table 3.

TABLE 1

ABSORPTION TEST DATA

| EXAMPLE | SUPERABSORBENT | WEIGHT | BASIS WEIGHT (g/m²) | DRY BULK (cc/g) | MAX CAPACITY (g/g) | MAX CAPACITY (g/m²) | WET BULK (cc/gm) | EXPANSION % |
|---|---|---|---|---|---|---|---|---|
| 1A | CONTROL* (None) | | 183 | 3.06 | 3.6 | 653 | 4.4 | 45 |
| 2A | SANWET IM-1500 | HEAVY | 385 | 4.84 | 21.3 | 8132 | 14.5 | 216 |
| 3A | | LIGHT | 262 | 6.11 | 17.9 | 4702 | 17.5 | 186 |
| 4A | NORSOCRYL B65 | HEAVY | 344 | 5.12 | 17.0 | 5849 | 16.9 | 233 |
| 5A | | LIGHT | 277 | 5.77 | 15.4 | 4266 | 24.3 | 320 |
| 1B | CONTROL** (None) | | 182 | 2.97 | 3.6 | 649 | 4.5 | 50 |
| 2B | SANWET-IM-1500 | HEAVY | 388 | 4.35 | 22.8 | 8840 | 14.7 | 238 |
| 3B | | LIGHT | 283 | 5.43 | 19.0 | 5386 | 15.8 | 191 |
| 4B | NORSOCRYL B65 | HEAVY | 350 | 4.41 | 14.2 | 4979 | 12.1 | 174 |
| 5B | | LIGHT | 246 | 6.03 | 14.6 | 3596 | 14.2 | 135 |

NOTE:
Control sample does not contain superabsorbent.
*Scrim size = 4 × 4 ends per inch.
**Scrim size = 6 × 3 ends per inch.

EXAMPLES 6-8

A composite laminate comprising a superabsorbent coated scrim sandwiched between two nonwoven webs

TABLE 2

| | | | ABSORPTION/RETENTION TEST DATA (WATER) | | | | | | | |
|---|---|---|---|---|---|---|---|---|---|---|
| EX-AMPLE | SUPER ABSORBENT | B.W. (G/SQ. M) | BULK (CC/G) | ABS. (G/G) | RET.* (G/G) | ABS/SQ. M (G/SQ. M) | INIT. RATE (G/G/SEC) | 50% RATE (G/G/SEC) | TIME (SEC) | EXPAND (%) |
| 6 | CONTROL | 21.7 | 6.70 | 6.11 | 0.32 | 132 | 90.2 | 48.1 | 271 | −5 |
| 7 | 19 | 28.5 | 4.62 | 13.24 | 9.36 | 378 | 125.8 | 49.9 | 245 | 137 |
| 8 | SA 7000 | 147.2 | 8.83 | 15.61 | 14.26 | 2,298 | 3.8 | 0.1 | 1,786 | 0 |

NOTE:
*Drainage stopped at 15 seconds for retention values. Surfactant in samples.

TABLE 3

| | | | ABSORPTION/RETENTION TEST DATA (SALINE) | | | | | | | |
|---|---|---|---|---|---|---|---|---|---|---|
| EX-AMPLE | SUPER ABSORBENT | B.W. (G/SQ. M) | BULK (CC/G) | ABS. (G/G) | RET.* (G/G) | ABS/SQ. M (G/SQ. M) | INIT. RATE (G/G/SEC) | 50% RATE (G/G/SEC) | TIME (SEC) | EXPAND (%) |
| 6A | CONTROL (none) | 23.5 | 6.71 | 6.95 | 0.21 | 163 | 91.9 | 49.0 | 321 | −9 |
| 7A | 19 | 29.4 | 4.60 | 6.09 | 3.69 | 179 | 45.6 | 22.7 | 459 | 33 |
| 8A | SA 7000 | 177.2 | 8.00 | 17.87 | 14.43 | 3,167 | 25.9 | 1.0 | 1,346 | 37 |

NOTE:
*Drainage stopped at 15 seconds for retention values. Surfactant in samples.

What is claimed is:

1. A method of making a liquid absorbent composite laminate having high wet strength and enhanced absorbency which comprises:
   (a) coating a scrim with a superabsorbent hydrophilic polymer, and
   (b) bonding the coated scrim to a nonwoven fibrous web.

2. The method of claim 1 wherein bonding is effected by applying an adhesive to the side of the nonwoven fibrous web which is brought into contact with the coated scrim and then heating the composite fibrous web and coated scrim bonding the web to the coated scrim.

3. The method of claim 1 wherein the scrim is wet with water and then coated with a powdered solid superabsorbent hydrophilic polymer prior to bonding the coated scrim to the nonwoven fibrous web.

4. The method of claim 3 wherein the water contains a water soluble adhesive.

5. The method of claim 1 wherein the superabsorbent coating and bonding is effected by coating the scrim with a liquid hydrophilic polymer, covering the coated scrim with the nonwoven fibrous web, and subjecting the hydrophilic polymer coating on said scrim to heat or ionizing radiation causing crosslinking of the polymer and bonding of the cellulosic web to the superabsorbent coated scrim.

6. The method of claim 5 wherein the scrim coated with liquid hydrophilic polymer is sandwiched between nonwoven fibrous webs prior to crosslinking of the polymer.

7. A liquid absorbent composite laminate having high wet strength and enhanced absorbency which comprises a scrim, a superabsorbent coating on said scrim, and a nonwoven fibrous web bonded to the said scrim.

8. A liquid absorbent composite laminate which comprises a scrim, a solid superabsorbent material coating at least one side of the scrim, and a nonwoven fibrous web bonded to the scrim and covering the superabsorbent material on the coated side of the scrim.

9. A liquid absorbent composite laminate as defined in claim 8 wherein both sides of the scrim are coated with a solid superabsorbent material and an absorbent nonwoven fibrous web is bonded to each side of the scrim.

10. A liquid absorbent composite laminate as defined in claim 7 wherein the scrim is a woven polyester screen and the fibrous web is an air laid cellulosic web.

11. A liquid absorbent composite laminate as defined in claim 7 wherein said superabsorbent coating on said scrim acts as a bonding agent between said scrim and said nonwoven fibrous web and is derived from a liquid polymer superabsorbent precursor.

12. A liquid absorbent composite laminate as defined in claim 7 wherein said nonwoven fibrous web is an absorbent cellulosic web.

13. A liquid absorbent composite laminate as defined in claim 7 wherein said nonwoven fibrous web is a relatively nonabsorbent web.

14. A liquid absorbent composite laminate as defined in claim 7 wherein said scrim has a basis weight in the range of from about 0.2 ounce per square yard to about 2 ounces per square yard.

15. A liquid absorbent composite laminate as defined in claim 11 wherein said superabsorbent material is a solid superabsorbent polymer produced by heating said liquid polymer after formation of the composite laminate.

16. A liquid absorbent composite laminate as defined in claim 11 wherein said superabsorbent material is a solid superabsorbent polymer produced by subjecting the composite laminate to ionizing radiation.

17. A liquid absorbent composite laminate as defined in claim 7 wherein said nonwoven fibrous web has a basis weight within the range of from about 10 pounds to about 50 pounds per 3000 sq. ft. ream.

18. A liquid absorbent composite laminate as defined in claim 7 wherein said nonwoven fibrous web is hydroentangled prior to bonding to said scrim.

* * * * *